US00PP24105P3

(12) United States Plant Patent
Smith

(10) Patent No.: US PP24,105 P3
(45) Date of Patent: Dec. 17, 2013

(54) *SALVIA* PLANT NAMED 'LEMON LIGHT'

(50) Latin Name: *Salvia hybrida*
Varietal Denomination: Lemon Light

(75) Inventor: M. Nevin Smith, Watsonville, CA (US)

(73) Assignee: CP Delaware, Inc., Wilmington, DE (US)

( * ) Notice: Subject to any disclaimer, the term of this patent is extended or adjusted under 35 U.S.C. 154(b) by 87 days.

(21) Appl. No.: 13/506,571

(22) Filed: Apr. 30, 2012

(65) Prior Publication Data

US 2013/0291267 P1 Oct. 31, 2013

(51) Int. Cl.
*A01H 5/00* (2006.01)

(52) U.S. Cl.
USPC ..... Plt./475

(58) Field of Classification Search
USPC ..... Plt./475
See application file for complete search history.

*Primary Examiner* — Annette Para
(74) *Attorney, Agent, or Firm* — Buchanan Ingersoll & Rooney PC

(57) ABSTRACT

A new and distinct *Salvia* plant of unknown parentage is provided that was discovered in a nursery setting while growing among other *Salvia* plants. Over a long blooming season in abundance attractive fully yellow blossoms are formed. The growth habit is compact and bushy. Attractive large bright green foliage is formed. Following pruning, the plant displays a tendency to vigorously regrow. The plant is well suited for providing attractive ornamentation.

2 Drawing Sheets

Botanical/commercial classification: *Salvia hybrida/ Salvia* Plant.

Varietal denomination: Cv. Lemon Light.

SUMMARY OF THE INVENTION

The new *Salvia* cultivar of the present invention was discovered while growing in a plant nursery setting among other *Salvia* plants at Watsonville, Calif., U.S.A. The new cultivar is of unknown parentage and likely includes *Salvia microphylla* in its ancestry. The new plant was distinguished from other *Salvia* plants growing in the nursery where it was discovered primarily through a study of its distinctive blossoms having a bright fully yellow coloration combined with other attractive botanical characteristics identified hereafter. Had the single plant of the present invention not been discovered and carefully preserved, it would have been lost to mankind.

The plant is a perennial that can be grown to advantage without protection in U.S.D.A. Hardiness Zone Nos. 7 to 11.

It was found that the new *Salvia* variety possesses the following combination of characteristics:

(a) displays a compact and bushy growth habit,
(b) forms in abundance over a long blooming season attractive fully yellow blossoms,
(c) displays vigorous large bright green leaves,
(d) displays a tendency to vigorously regrow following pruning, and
(e) is well suited for providing attractive ornamentation.

The new cultivar of the present invention can be readily distinguished from other *Salvia* cultivars, such as the 'Golden Girl' variety (U.S. Plant patent application Ser. No. 12/923,371, filed Sep. 17, 2010). More specifically, the blossoms of the new variety are brighter yellow in coloration and lack Red-Purple coloration at the apex of the upper lobe that is a characteristic of the 'Golden Girl' variety.

The new cultivar well meets the needs of the horticultural industry and can be grown to advantage as attractive ornamentation in parks, gardens, public areas, and residential landscapes.

The new cultivar has been asexually reproduced by the rooting of cuttings for several generations. Such asexual reproduction as performed at Watsonville, Calif., U.S.A., and near West Grove, Pa., U.S.A., has demonstrated that the characteristics of the new cultivar are firmly fixed and stable and are strictly transmissible from one generation to another. Accordingly, the new cultivar asexually reproduces in a true-to-type manner from one generation to another.

The new cultivar has been named 'Lemon Light'.

BRIEF DESCRIPTION OF THE PHOTOGRAPHS

The accompanying photographs show the new variety as nearly true as it is reasonably possible to make the same, in color illustrations of this character. The photographs were obtained on Apr. 17, 2012 near West Grove, Pa., U.S.A., and illustrate a typical container grown plant and plant parts of the new variety.

DETAILED BOTANICAL DESCRIPTION

Figure 1:
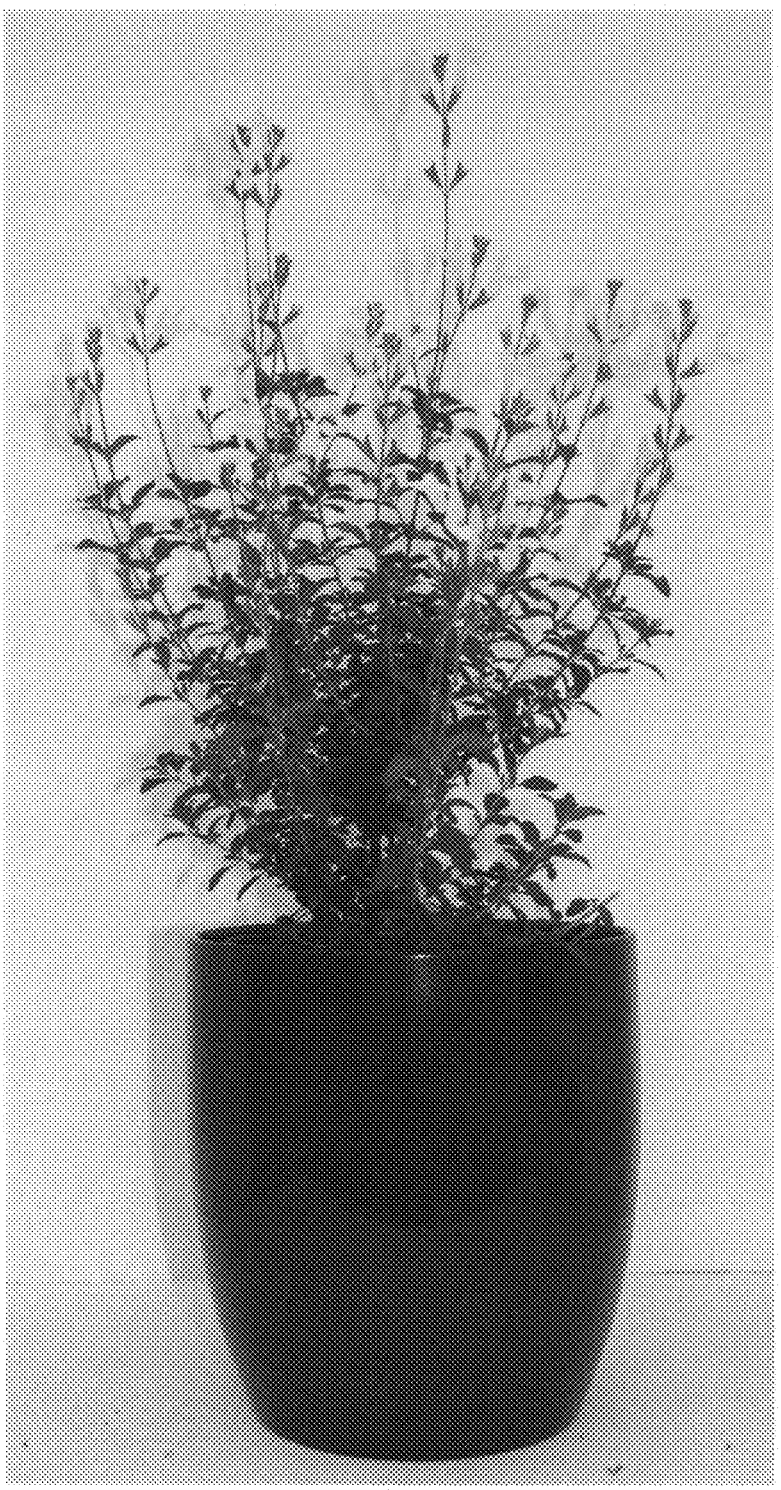
FIG. 1 illustrates the overall compact growth habit of a flowering plant of the new variety.
Figure 2:
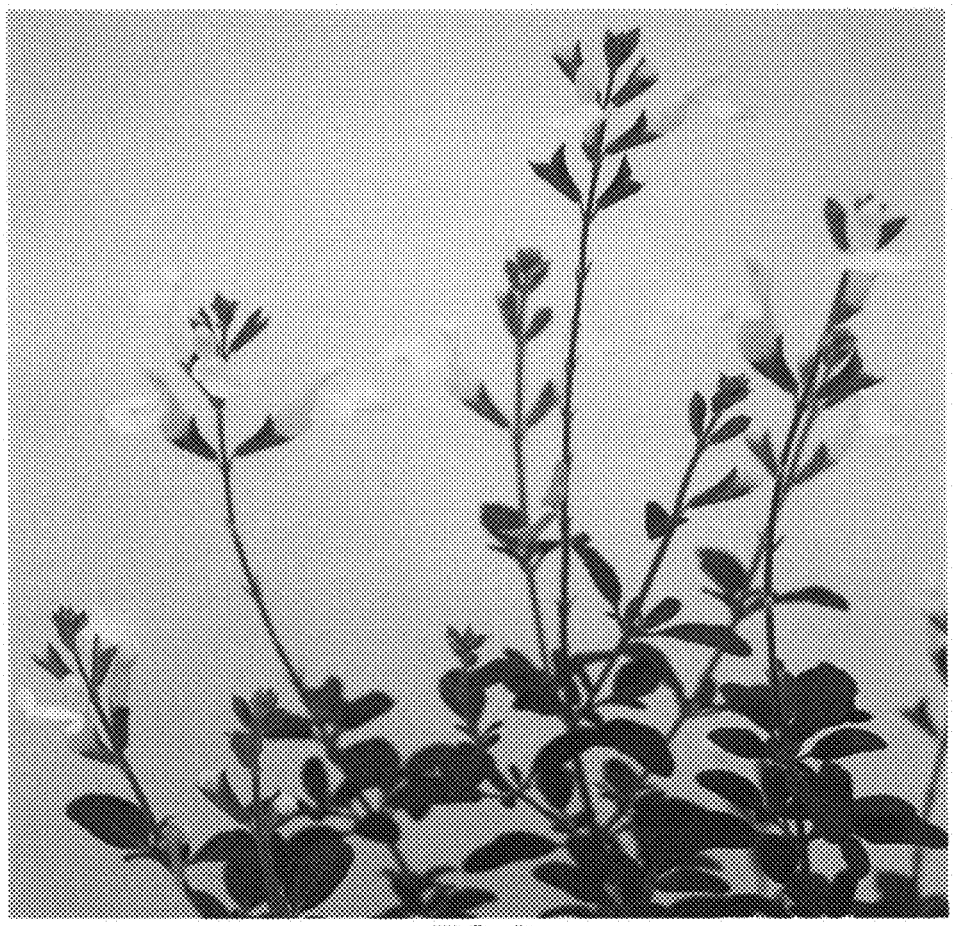
FIG. 2 illustrates a closer view of the foliage and the fully yellow blossoms of the new variety.

The chart used in the identification of colors is that of The Royal Horticultural Society (R.H.S. Colour Chart) of London, England (1995). Color terminology in common terms sometimes is included as an aid to the reader. Such color terminology is to be accorded its customary dictionary significance. The description is based on the observation of typical specimens of the new variety at an age of approximately one year during April 2012 while growing indoors in containers under natural light near West Grove, Pa., U.S.A.

Plant:

*Form.*—Bushy, vigorous, and compact.

*Height.*—Commonly up to approximately 45 cm on average.

*Width.*—Commonly approximately 46 cm on average.

*Growth habit.*—Perennial in U.S.D.A. Hardiness Zone Nos. 7 to 11.

*Leaf arrangement.*—Opposite.

*Leaf configuration.*—Elliptic to oblong.

*Leaf length.*—Commonly approximately 1.9 cm on average.

*Leaf width.*—Commonly approximately 1.3 cm on average.

*Leaf margin.*—Repand.

*Leaf texture.*—Commonly slightly fleshy.

*Leaf blade color.*—Green Group 137A on the upper surface, and Green Group 137C on the under surface. Newer growth commonly is overlaid with Yellow-Green Group 144B on the upper surface.

*Leaf blade apex.*—Acute to obtusely rounded.

*Leaf blade base.*—Mainly obtuse.

*Scent.*—Leaves commonly display a tangy fruity scent when crushed.

*Petiole shape.*—Somewhat flattened.

*Petiole length.*—Variable and commonly approximately 5 mm.

*Petiole width.*—Commonly approximately 1 mm.

*Petiole color.*—Yellow-Green Group 144C.

Inflorescence:

*Time.*—Prolonged blooming period beginning in May and extending through September near West Grove, Pa., U.S.A.

*Type.*—Terminal raceme.

*Shape.*—Tubular, two lipped.

*Diameter.*—Commonly approximately 5 cm on average.

*Length.*—Commonly approximately 16 cm on average.

*Number.*—Commonly up to approximately 93 flowers per plant on average in bloom at a given time.

*Configuration.*—Tubular, and two-lipped.

*Pedicel length.*—Commonly approximately 4 mm on average.

*Pedicel width.*—Commonly approximately 1 mm on average.

*Pedicel color.*—Green, Yellow-Green Group 145B.

*Pedicel pubescence.*—None observed.

*Calyx shape.*—Broadly campanulate and flared towards the apex.

*Calyx rib number.*—Commonly 14 and longitudinally disposed.

*Calyx length.*—Commonly approximately 11 mm on average.

*Calyx width.*—Commonly up to 8 mm.

*Calyx texture.*—Glandular and puberulent on the upper and under surfaces.

*Calyx color.*—On the upper lobe Green Group 143B, and on the lower lobes Yellow-Green Group 144C.

*Calyx lobe number.*—3.

*Calyx upper lobe number.*—1.

*Calyx upper lobe shape.*—Acute.

*Calyx upper lobe length.*—Commonly approximately 1.1 cm on average.

*Calyx upper lobe width.*—Commonly approximately 4 mm in width.

*Calyx lower lobe number.*—2.

*Calyx lower lobe shape.*—Acute.

*Calyx lower lobe length.*—Commonly approximately 1.1 cm on average.

*Calyx lower lobe width.*—Commonly approximately 6 mm on average.

*Corolla shape.*—Tubular proximally to two-lipped distally.

*Corolla length.*—Commonly approximately 1 cm on average.

*Corolla color.*—The base commonly is White Group 155A, the tube is near Yellow Group 2C, and the lower lip is near Yellow Group 2B. Red-Purple coloration is absent on the upper lobe.

*Corolla tube length.*—Approximately 18 mm on average.

*Corolla tube depth.*—Approximately 7 mm on average.

*Corolla tube lip number.*—3.

*Corolla upper lip number* 1.

*Corolla upper lip shape.*—Hood-like.

*Corolla upper lip length.*—Commonly approximately 10 mm average.

*Corolla lower lip length.*—2, suborbicular.

*Corolla lower lip shape.*—Banner-like, and extended downward.

*Corolla lower lip outline.*—Obovate.

*Corolla lower lip length.*—Commonly approximately 14 mm on average.

*Corolla lower lip diameter at tip.*—Approximately 16 mm on average.

*Style length.*—Approximately 2.4 cm on average.

*Style width.*—Commonly less than 1 mm on average.

*Style color.*—White Group 155A.

*Style attachment site.*—At four-lobed ovary between lobes.

*Ovary.*—Approximately 2 mm in length, approximately 2 mm in diameter, and near Yellow-Green Group 150B in coloration.

*Stamen number.*—1.

*Stamen shape.*—Seesaw-like.

*Filament length.*—Approximately 6 mm on average.

*Connective length.*—Approximately 7 mm on average.

*Anther length.*—Approximately 1 mm on average.

*Anther diameter.*—Less than 1 mm on average.

*Anther color.*—Greyed-Orange Group 163B.

*Anther attachment site.*—At outer end of the connective.

*Pollen.*—Abundant.

Development:

*Vegetation.*—Vigorous and displays a tendency to quickly regrow following pruning.

*Blooming.*—Displays long blooming season.

*Fertility.*—Not observed with the plants being sterile during observations to date.

*Winter hardiness.*—The plant is a perennial that can be grown in at least U.S.D.A. Hardiness Zone Nos. 7 to 11.

*Disease resistance.*—No particular sensitivity to disease has been encountered during observations to date.

I claim:

1. A new and distinct *Salvia* plant characterized by the following combination of characteristics:

(a) displays a compact and bushy growth habit, (b) forms in abundance over a long blooming season attractive fully yellow blossoms, (c) displays vigorous large bright green leaves, (d) displays a tendency to vigorously regrow following pruning, and (e) is well suited for providing attractive ornamentation; substantially as illustrated and described.

* * * * *